US010145803B2

(12) United States Patent
Bloomberg et al.

(10) Patent No.: US 10,145,803 B2
(45) Date of Patent: Dec. 4, 2018

(54) PH COLOUR INDICATOR FOR USE WITH AGRICULTURAL COMPOUNDS

(75) Inventors: Martin David Bloomberg, Toronto (CA); Mark Stewart Houston-McMillan, Toronto (CA)

(73) Assignee: NUTRIAG LTD., Toronto (CA)

( * ) Notice: Subject to any disclaimer, the term of this patent is extended or adjusted under 35 U.S.C. 154(b) by 1321 days.

(21) Appl. No.: 10/570,048

(22) PCT Filed: Aug. 24, 2004

(86) PCT No.: PCT/CA2004/001555
§ 371 (c)(1),
(2), (4) Date: Dec. 12, 2006

(87) PCT Pub. No.: WO2005/018334
PCT Pub. Date: Mar. 3, 2005

(65) Prior Publication Data
US 2007/0111892 A1  May 17, 2007

Related U.S. Application Data

(63) Continuation of application No. 10/646,928, filed on Aug. 25, 2003.

(51) Int. Cl.
*G01N 30/90* (2006.01)
*G01N 21/80* (2006.01)
*A01N 65/00* (2009.01)
*C05G 3/00* (2006.01)
*A01N 65/03* (2009.01)
*A01N 65/08* (2009.01)

(52) U.S. Cl.
CPC ............ *G01N 21/80* (2013.01); *A01N 65/00* (2013.01); *A01N 65/03* (2013.01); *A01N 65/08* (2013.01); *C05G 3/00* (2013.01)

(58) Field of Classification Search
CPC ........ G01N 21/80; A01N 65/08; A01N 65/03; A01N 65/00; A01N 61/00; A01N 63/02; C05G 3/00
USPC .......................................... 436/163; 116/206
See application file for complete search history.

(56) References Cited

U.S. PATENT DOCUMENTS

| | | | |
|---|---|---|---|
| 4,939,086 A * | 7/1990 | Vunsh et al. | 435/67 |
| 5,278,132 A * | 1/1994 | Fisher et al. | 504/124 |
| 6,036,666 A | 3/2000 | Peiler | |
| 6,132,791 A * | 10/2000 | Fox | 426/540 |
| 6,589,761 B1 * | 7/2003 | Freadman et al. | 435/29 |
| 2001/0012636 A1 * | 8/2001 | Azar et al. | 436/163 |
| 2004/0121050 A1 * | 6/2004 | Thurman | A23G 9/045 426/120 |
| 2005/0233919 A1 * | 10/2005 | Rich | 510/136 |

FOREIGN PATENT DOCUMENTS

| | | |
|---|---|---|
| EP | 760482 | 3/1997 |
| WO | WO 99/25189 | 5/1999 |
| WO | WO 2004/025254 | 3/2004 |

OTHER PUBLICATIONS

Daniela Brotto Lopes Terci et al, "Indicadores Naturais de pH: usar papel ou solucao?" Quimica Nova, vol. 25, No. 4, Jul. 2002.*
http://scifun.chem.wisc.edu/HOMEEXPTS/ACIDBASE.html, Nov. 4, 2013.*
Zumdahl, Steven S., Chimie (chimie des solutions); textbook; Ed. Centre Educatif et Culturel inc., Montreal, 381 pages, 1998, p. 218.
Bakowska-Barczak et al.; Acylated Anthocyanins as Stable, Natural Food Colorants—A Review; Pol. J. Food Nutr. Sci.; 2005, vol. 14/55, No. 2, pp. 107-116.
Charron et al.; Effect of Dose Size on Bioavailability of Aclated and Nonacylated Anthocyanins from Red Cabbage (Brassica oleracea L. Var. Capitata); Journal of Agricultural and Food Chemistry 2007, 55, 53545362.
Dao et al.; Improved Method for the Stabilization of Anthocyanidins; J. Agric. Food Chem. 1998, 46, 35643569.
Davies et al.; Copigmentation of Simple and Acylated Anthocyanins with Colorless Phenolic Compounds, J. Agric. Food. Cehm. 1993, 41, 716-720.
Dyrby et al.; Light and heat sensitivity of red cabbage extract in soft drink model systems; Food Chemistry 72 (2001) 434-437.
Huang et al.; Identification of anthocyanins in muscadinegrapes with HPLC-ESI-MS; LWT—Food Science and Technology 42 (2009) 819-824.
Inert Ingredients Permitted for Use in Nonfood Use Pesticide Products; United States Environmental Protection Agency; Last updated Apr. 2011; 77 pgs.
Kong et al.; Analysis and biological activities of anthocyanins; Phytochemistry 63 (2003) 923933.
Malien-Aubert et al.; Color Stability of Commercial AnthocyaninBased Extracts in Relation to the Phenolic Composition. Protective Effects by Intra and Intermolecular Copigmentation; J. Agric. Food Chem. 2001, 49, 170176.
Pinheiro et al.; Total Phenolics and Total Anthocyanins Found in Grape form Benitaka Cultivar; Journal of Food Technology 7 (3); 78-83, 2009.

(Continued)

*Primary Examiner* — Dennis White
(74) *Attorney, Agent, or Firm* — Bereskin & Parr LLP/S.E.N.C.R.L.,S.R.L.; Patricia Folkins

(57) ABSTRACT

This invention discloses a new class of pH indicators suitable for use in agricultural compounds. The class comprises naturally occurring substances which are extracts from grape skins, cabbage and lecithin. Safety concerns are now causing regulatory bodies to prohibit use of chemical pH indicators in compounds which are used for crops and animals. The naturally occurring compounds of this invention satisfy these concerns of the regulators and function as well as chemical indicators of the prior art.

8 Claims, No Drawings

(56) References Cited

OTHER PUBLICATIONS

Puntener et al.; Europoean Ban on Certain Azo Dyes; www.tfl.com; Jan. 5, 2004; pp. 1-6.

Revilla et al.; Comparison of Several Procedures Used for the Extraction of Anthocyanins from Red Grages; J. Agric. Food Chem. 1998; 46, 4592-4597.

* cited by examiner

PH COLOUR INDICATOR FOR USE WITH AGRICULTURAL COMPOUNDS

This invention relates to agricultural compounds and more particularly to an improved agricultural compound which uses a naturally occurring pH indicator rather than a chemical pH indicator.

DESCRIPTION OF THE PRIOR ART

U.S. Pat. No. 5,278,132 granted to Gouws & Scheepers (Proprietary) Limited discloses a concentrate for dilution with water useful in the production of agricultural compounds for application to crops, soil or animals. The concentrate is added to the agricultural compound and then diluted with water until the desired pH is reached. This desired level of pH is controlled by the agricultural compound.

The patent discloses several chemicals which are used to determine the level of pH. These compounds include methyl red, resorcin blue, 2,5-dinitrophenol and chlorophenol red. These pH indicators change colour when the pH is changed and accordingly, provide a visual indicator as to when the desired pH is reached.

However, regulatory authorities throughout the world are now discouraging the use of non-natural ingredients especially when the agricultural compounds are used on crops and for treatment of animals. As a result, the chemical pH indicators currently in use are being rejected by regulatory authorities.

The Food and Drug Agency of the United States government sets out specifications of products which are approved for such use. These specifications are contained in, inter alia, Federal regulations, Title 21, Part 73.170. It is noted that methyl red is not listed and is therefore not an approved product.

Similarly, the European Economic Commission has also issued directives as contained in the EEC Additives No. E163 (Commission directive 95/45/EC as amended) which lists approved products for such use.

BRIEF DESCRIPTION OF THE INVENTION

Accordingly, the present invention provides an improvement wherein a completely naturally occurring product is used as the pH indicator.

To this end, in one of its aspects, the invention provides a naturally occurring pH indicator for use in a concentrate for preparing an agricultural compound which comprises an extract from grapes, cabbage or lichen.

In another of its aspects, the invention provides a concentrate comprising a mixture of a pH modifying agent and a naturally occurring pH indicator for colouring water, which concentrate can be diluted with water and added to an agricultural chemical for application to crops, soil or animals, the agricultural chemical having an activity that varies with the pH of the water and having an acceptable agricultural activity at a pH within the range of 4-6, wherein the proportions of pH modifying agent and pH indicator in the concentrate are such that when the concentrate is diluted with water and the pH of the water is modified by the pH modifying agent, the pH indicator indicates visually when the pH of the water is in the range of from about 4 to about 6.

DESCRIPTION OF THE PREFERRED EMBODIMENT

The inventors have discovered that several naturally occurring products may be used as the colour/pH indicator in the concentrate as disclosed in U.S. Pat. No. 5,278,132. These naturally occurring compounds produce the same colour changes as do the chemical compounds but are acceptable to regulatory authorities throughout the world. These compounds exhibit no untoward activity to plants or animals.

The pH indictor of the present invention is selected from the group consisting of extracts from grape skins, cabbage or lichen. Extracts of grape skins are preferred because the required concentration is less but extracts of cabbage and lichen are also acceptable although they do require a higher concentration.

It is desired that the pH indicator change colour at a pH from about 4 to about 6. It is also desired that the indicator not have any deleterious effects on the crops or animals and it is for this reason that the naturally occurring products of the invention are so useful.

The grapes are first processed to remove the juice from the grapes to produce grape juice or wine and then the skin of the grape is removed. The grape skin extract is a purplish-red liquid which is prepared by the aqueous extraction of the fresh deseeded marc remaining after the grapes have been pressed. The extract contains anthocyanins, tartaric acid, tannins, sugars and minerals but not in the same proportions as in the grape juice. During the steeping process, sulphur dioxide is added and most of the extracted sugars are fermented to alcohol. The extract is then concentrated by vacuum evaporation during which almost all of the alcohol is removed. A small amount of sulphur dioxide may be present.

The extract shows a blue colour at a pH greater than 5 and a red colour at a pH lower than 5.

This extract was tested in the formulations disclosed in U.S. Pat. No. 5,278,132 and excellent results were obtained. However, it was found that much higher concentrations were required to show the visual colour change. Concentrations in the range of 10 to 25% were necessary to show the colour changes.

The experiments were repeated using cabbage extract and lichen extract. These worked although higher concentrations were necessary. Thus, while they clearly fall within the scope of this invention, the preferred product is grape extract.

An example of the concentrate (acid adjuvant) suitable for pH reduction, control and buffering in aqueous agricultural compositions for application to plants or soil an alkali sensitive agricultural chemicals subject to degradation in alkaline environments was formulated with the following composition:

| | |
|---|---|
| Nonyl phenoxy polyoxyethylene glycol | 10.4 |
| Monoortho-phosphoric esters | 43.6 |
| Diorthophosphoric esters | 2.9 |
| Isopropyl alcohol | 15.6 |
| Water | 17.5 |
| Grape skin extract | 10.0 |

All percentages are expressed in mass/mass.

A second example of the concentrate (acid adjuvant) suitable for pH reduction, control and buffering in aqueous agricultural compositions for application to plants or soil an alkali sensitive agricultural chemicals subject to degradation in alkaline environments was formulated with the following composition:

|   |   |
|---|---|
| Nonyl phenoxy polyoxyethylene glycol | 10.4 |
| Monoortho-phosphoric esters | 43.6 |
| Diorthophosphoric esters | 2.9 |
| Isopropyl alcohol | 15.6 |
| Cabbage Extract | 27.5 |

All percentages are expressed in mass/mass.

A third example of the concentrate (acid adjuvant) suitable for pH reduction, control and buffering in aqueous agricultural compositions for application to plants or soil an alkali sensitive agricultural chemicals subject to degradation in alkaline environments was formulated with the following composition:

|   |   |
|---|---|
| Nonyl phenoxy polyoxyethylene glycol | 10.4 |
| Monoortho-phosphoric esters | 43.6 |
| Diorthophosphoric esters | 2.9 |
| Isopropyl alcohol | 15.6 |
| Lichen extract | 27.5 |

All percentages are expressed in mass/mass.

Accordingly, the use of a naturally occurring pH indicator represents a significant advance.

Although the invention describes and illustrates a preferred embodiment of the invention, kit is understood that it is no so restricted and includes in its scope, variations thereof.

We claim:

1. A method for preparing an agricultural composition which is suitable for application to crops, soil or animals and is added to an agricultural chemical with an activity which varies with pH, the method comprising:
   diluting a liquid concentrate comprising a mixture of an acidic pH modifying agent and a naturally occurring pH indicator for coloring water, with water, wherein the naturally occurring pH indicator consists of a naturally occurring pH indicator from cabbage and the proportions of pH modifying agent and pH indicator in the concentrate are such that when the concentrate is diluted with the water and the pH of the water is modified by the pH modifying agent, the pH indicator indicates visually when the pH of the water is in the range of from about 4 to about 6;
   wherein diluting said concentrate with the water effects a color change of the pH indicator in the concentrate.

2. The method according to claim 1 wherein the concentrate comprises 10.4% by weight of the concentrate of nonyl phenoxy polyoxyethylene glycol, 43.6% by weight of the concentrate of monoortho-phosphoric esters, 2.9% by weight of the concentrate of diorthophosphoric esters, and 15.6% by weight of the concentrate of isopropyl alcohol.

3. A method for preparing an agricultural composition which is suitable for application to crops, soil or animals, the method comprising:
   diluting a concentrate with water, wherein the concentrate is a liquid concentrate comprising a mixture of an acidic pH modifying agent and a naturally occurring pH indicator from cabbage,
   wherein the pH modifying agent, when the concentrate is diluted with the water and added to an agricultural chemical for application to crops, soil or animals, modifies the pH of the water, and
   wherein the naturally occurring pH indicator from cabbage, when the concentrate is diluted with water, indicates visually by a color change when the pH of the water is in the range of about 4 to about 6.

4. The method for preparing an agricultural composition which is suitable for application to crops, soil or animals of claim 3, wherein the naturally occurring pH indicator from cabbage is present in an amount of 27.5% by weight of the concentrate.

5. The method of claim 3, wherein the proportions of pH modifying agent and pH indicator in the concentrate are such that when the concentrate is diluted with the water and the pH of the water is modified by the pH modifying agent, the pH indicator indicates visually by a color change when the pH of the water is in the range of from about 4 to about 6.

6. A method for preparing an agricultural composition which is suitable for application to crops, soil or animals, the method comprising:
   diluting a concentrate with water, wherein the concentrate is a liquid concentrate comprising a mixture of an acidic pH modifying agent and a naturally occurring pH indicator from cabbage,
   wherein the pH modifying agent, when the concentrate is diluted with the water and added to an agricultural chemical for application to crops, soil or animals, modifies the pH of the water, and
   wherein the naturally occurring pH indicator from cabbage, when the concentrate is diluted with water, indicates visually by a color change when the pH of the water is in the range of about 4 to about 6; and
   adding to the diluted concentrate an agricultural chemical having an activity that varies with the pH of the agricultural composition and having an acceptable agricultural activity at a pH within the range of 4-6.

7. The method of claim 6, wherein the proportions of pH modifying agent and pH indicator in the concentrate are such that when the concentrate is diluted with the water and the pH of the water is modified by the pH modifying agent, the pH indicator indicates visually by a color change when the pH of the water is in the range of from about 4 to about 6.

8. The method for preparing an agricultural composition which is suitable for application to crops, soil or animals of claim 6 wherein the naturally occurring pH indicator from cabbage is present in an amount of 27.5% by weight of the concentrate.

* * * * *